United States Patent [19]

Milzner

[11] 4,400,201

[45] Aug. 23, 1983

[54] NOVEL PYRIMIDINYL ETHERS, THEIR USE AS HERBICIDES, HERBICIDAL COMPOSITIONS COMPRISING SAID PYRIMIDINYL ETHERS AND PROCESSES FOR THE PREPARATION THEREOF

[75] Inventor: Karlheinz Milzner, Basel, Switzerland

[73] Assignee: Sandoz Ltd., Basel, Switzerland

[21] Appl. No.: 329,260

[22] Filed: Dec. 10, 1981

[30] Foreign Application Priority Data

Dec. 15, 1980 [GB] United Kingdom ............... 8040074

[51] Int. Cl.$^3$ ..................... A01N 9/22; C07D 239/47
[52] U.S. Cl. ........................................ 71/92; 544/321
[58] Field of Search ........................... 544/321; 71/92

[56] References Cited

U.S. PATENT DOCUMENTS 4,116,674  9/1978  Sunley ..................................... 71/92

Primary Examiner—Robert Gerstl
Attorney, Agent, or Firm—Richard E. Vila; Gerald D. Sharkin

[57] ABSTRACT

Pyrimidines having an amino group in the 2-position and a cyclopropylmethoxy group in the 4-position of the pyrimidine nucleus. Compounds according to the invention have valuable herbicidal activity, particularly after pre-emergence application in cotton and sunflower.

7 Claims, No Drawings

NOVEL PYRIMIDINYL ETHERS, THEIR USE AS HERBICIDES, HERBICIDAL COMPOSITIONS COMPRISING SAID PYRIMIDINYL ETHERS AND PROCESSES FOR THE PREPARATION THEREOF

The present invention relates to pyrimidinyl ethers, their use as herbicides, compositions for facilitating such use and the preparation of the novel compounds and compositions of the invention.

The U.K. Pat. No. 1,523,274 discloses i.a. 2-amino-4-pyrimidinyl ethers having herbicidal activity. Although a wide variety of herbicides is available, the need exists for still more effective or selective herbicides.

The present invention provides novel 2-amino-4-pyridimidinyl ethers characterised by having a cyclopropylmethoxy group in the 4-position of the pyrimidine nucleus.

The amino group in the 2-position of the pyrimidine nucleus may be any herbicidally acceptable primary, secondary or tertiary amino group.

The cyclopropylmethoxy group in the 4-position of the pyrimidine nucleus may be unsubstituted or substituted in the cyclopropyl moiety by a herbicidally acceptable group.

The pyrimidine nucleus may further bear herbicidally acceptable substituents in the 5- and 6-position.

The compounds of the invention may be in the form of acid addition salts. Any salt form of compounds of the invention is preferably in the form of an herbicidally acceptable salt form. The acid addition salt forms can be prepared from the free base form in conventional manner and vice versa. Examples of acids which may be used to form suitable acid addition salts include hydrochloric, hydrobromic, sulphuric, nitric and phosphoric acids.

A particular group of compounds of the invention are those of formula I

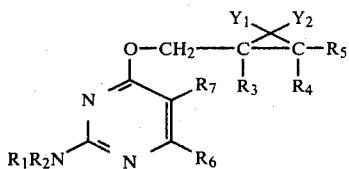

wherein
either $R_1$ is H or $(C_1-C_{18})$alkyl, $(C_1-C_{18})$alkyl substituted by up to 2 substituents selected from $(C_1-C_4)$alkoxy or 2-tetrahydrofuryl; $(C_1-C_{18})$alkenyl; $(C_3-C_8)$cycloalkyl or $(C_3-C_8)$cycloalkyl-$(C_1-C_5)$alkyl, unsubstituted or substituted by up to 2 halogens selected from fluorine, chlorine and bromine; phenyl unsubstituted or substituted by up to 3 substituents selected from halogen of the group fluorine, chlorine and bromine, $(C_1-C_4)$alkyl and $(C_1-C_4)$alkoxy;
and $R_2$ is H, $(C_1-C_5)$alkyl,
or $R_1$ and $R_2$ together are a $(C_4-C_6)$alkylene chain,
$Y_1$ and $Y_2$ independently are H or halogen selected from fluorine, chlorine or bromine,
$R_3, R_4$ and $R_5$ independently are H, $(C_1-C_5)$alkyl unsubstituted or substituted by halogen selected from fluorine, chlorine or bromine,
$R_6$ is $(C_1-C_5)$alkyl, and
$R_7$ is H or $(C_1-C_5)$alkyl.

Where $R_1$ is $(C_1-C_{18})$alkyl, unsubstituted or substituted, it may be branched or straight chained. Branched $(C_1-C_{18})$-alkyl have preferably a secondary C-atom in α-position of the N-atom to which they are bound. Especially preferred $(C_1-C_{18})$alkyl are $(C_1-C_{12})$alkyl, particularly ethyl, n-propyl, isopropyl, n-butyl, sec. butyl, 1-methyl-butyl-1,n-hexyl, 1-methyl-heptyl-1 and n-decyl. When $R_1$ is substituted, it is preferably mono-substituted.

Preferred substituents include $CH_3O$ and 2-tetrahydrofuryl.

Where $R_1$ is $(C_1-C_{18})$alkenyl, it may be branched or straight chained and is preferably $(C_1-C_{12})$alkenyl, e.g. allyl.

Where $R_1$ is or contains $(C_3-C_8)$cycloalkyl, this is preferably $(C_3-C_6)$cycloalkyl, more preferably $(C_3-C_5)$cycloalkyl. Where $R_1$ is $(C_3-C_8)$cycloalkyl$(C_1-C_5)$-alkyl the alkylene moiety thereof has preferably 1 to 3 C-atoms, and is more preferably $CH_2$.

Where $R_1$ is $(C_3-C_8)$cycloalkyl or $(C_3-C_8)$cycloalkyl-$(C_1-C_5)$alkyl substituted by halogen, the halogen is preferably Cl or Br, particularly Cl and is preferably in the cycloalkyl moiety of the group.

Where $R_1$ is substituted phenyl as defined hereinabove, the halogen substituent thereof is preferably Cl, and the $(C_1-C_4)$alkyl or $(C_1-C_4)$alkoxy substituents have preferably 1-2 C-atoms, more preferably 1 C-atom. The substituted phenyl group is preferably mono-substituted.

$R_1$ is preferably $(C_{3-6})$alkyl, particularly $(C_{3-4})$alkyl, especially when in branched form.

$R_2$ is preferably H or $CH_3$, particularly H.

Where $Y_1$ and/or $Y_2$ are halogen, the halogen is preferably Cl or Br. $Y_1$ and $Y_2$ are preferably identical.

Where any of $R_3$, $R_4$ and $R_5$ is $(C_1-C_5)$alkyl, it is preferably $(C_1-C_4)$alkyl, more preferably $(C_1-C_2)$alkyl, particularly methyl. Where any of these $R_3$, $R_4$ or $R_5$ is substituted by halogen, it is preferably monosubstituted, preferably by Cl or Br, particularly by Cl.

Where $R_6$ and/or $R_7$ are $(C_1-C_5)$alkyl, they may be branched or straight chained and are preferably methyl.

$R_7$ is preferably hydrogen.

A preferred sub-group of the compounds of formula I is represented by formula Ia,

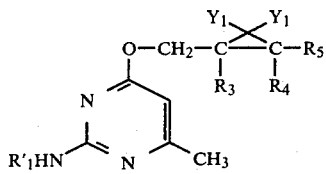

wherein
$R_1'$ is $(C_1-C_{18})$alkyl and
$Y_1, R_3, R_4$ and $R_5$ are as defined above.

The present invention also provides a process for producing a compound of the invention which comprises linking the desired cyclopropylmethyl group to the oxygen of the corresponding 4-hydroxypyrimidine, or the alkali metal salt thereof, by O-alkylation techniques. For example, a compound of formula I may be obtained by O-alkylating a compound of formula II

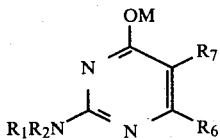

wherein

M is H or an alkali metal, and $R_1$, $R_2$, $R_6$ and $R_7$ are as defined above, with a compound of formula III

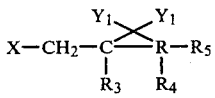

wherein

X is a leaving group displaceable under the reaction conditions and $Y_1$, $Y_2$, $R_3$, $R_4$ and $R_5$ are as defined above.

The above process may be carried out in conventional manner under conditions known for the preparation of 4-pyrimidinyl ethers from 4-hydroxypyrimidines or their corresponding alkali metal salts.

X can be any leaving group displaceable under 4-hydroxy-pyrimidine condensing reaction conditions and is preferably halogen selected from chlorine and bromine, particularly chlorine.

Where M is an alkali metal it is preferably Na or K.

The reaction may be carried out in the absence or presence of a solvent, preferably in a solvent. Where a solvent is used, such is preferably an amide of an organic carboxylic acid such as dimethylformamide, a hydrocarbon, a chlorinated hydrocarbon, an ether or ketone, an alcohol or pyridine. A suitable reaction temperature is from 0° to 150° C. preferably from 40° to 120° C. Where M is hydrogen, the reaction is preferably carried out in the presence of an acid binding agent such as potassium or sodium carbonate, potassium hydroxide, sodium methoxide, triethylamine or pyridine.

When the O-alkylation is effected in the presence of an alkali metal base, the compound of formula II will, at least partially, react as alkali metal salt.

Depending on the meaning of the substituents, the compounds of formula I can occur in different isomeric forms. When mixtures of isomeric compounds are produced, it is, as a practical matter, generally preferred to employ such mixtures as such in the herbicide method and compositions of the invention, even though separation may be effected by known procedures.

The compounds of the invention are useful as herbicides, whereby herbicide as used herein means a compound which controls or modifies the growth of a vegetation or plants. By plants it is meant germinant seeds, emerging seedlings and established vegetation including underground portions.

The useful herbicidal activity of the compounds of the invention is indicated by i.a. the damage caused to both monocotyledoneous and dicotyledoneous weeds such as *Lepidium sativum, Avena sativa, Agrostis alba* and *Lolium perenne* in tests by test dosages equivalent to an application rate of from 1.4 to 5.6 kg/ha after pre- or post-emergence application. In view of their herbicidal effect the compounds of the invention are indicated for use in combatting dicotyledoneous and grassy weeds, as confirmed by further evaluation with representative compounds with test dosages equivalent to an application rate of from 0.15 to 5.0 kg active ingredient, e.g. test dosages as indicated hereinafter in the examples, in dicotyledoneous weeds such as *Amaranthus retroflexus, Capsella bursa-pastoris, Chenopodium alba, Stellaria media, Senecio vulgaris, Galium aparine,* Portulaca spp and Abutilon spp. and, especially, grassy weeds such as *Agropyron repens, Agrostis alba, Alopecurus myosuroides, Apera spica venti, Avena fatua, Echinochloa crus-galli, Lolium perenne, Sorghum halepense, Digitaria sanguinalis, Setaria italica, Leptochloa dubia* and Panicum spp.

The compounds of the invention are relatively less toxic towards e.g. grassy crops such as a small grain (wheat, barley, upland rice, paddy rice) or corn or against broad leaved crops such as soya, cotton, carrot, sugar beet, potato, alfalfa, sunflower or flax than towards weeds. The compounds of the invention are therefore also indicated for use as selective herbicides in a crop locus.

The present invention therefore also provides a method of combatting weeds in a locus, preferably in a crop locus as mentioned above, which comprises applying to the locus a herbicidally effective amount of a compound of the invention.

For general herbicidal as well as for selective herbicidal use of compounds of the invention, the amount to be applied to attain the desired effect will vary depending on the particular crop if employed for selective use and other standard variables such as the compound employed, mode of application, conditions of treatment and the like. The appropriate application rates can be determined by routine procedures by those skilled in the art, or by comparing the activity of the compounds of the invention with standards for which the application rate is known, e.g. in greenhouse tests. However, in general, satisfactory results are usually obtained when the compound is applied at a rate in the range of from about 0.2 to 5 kg/ha, preferably from about 0.5 to 4 kg/ha, more preferably from 1.0 to 3.0 kg/ha, the application being repeated as necessary. When used in a crop locus, the application rate should preferably not exceed 3 kg/ha.

An embodiment of the invention is the post-emergence use of the compounds of the invention in selectively combatting weeds in dicotyledoneous crops such as alfalfa, potato, sunflower and carrot, preferably the latter and, particularly, in grassy crops such as cereals (wheat etc.) and corn (maize).

A further preferred and advantageous embodiment of the invention is the pre-emergence use of the compounds of the invention in selectively combatting weeds in dicotyledoneous crops such as carrot, potato, soya, alfalfa, sunflower and cotton.

Particularly preferred is the pre-emergence use of the compounds of the invention in sunflower and, especially, in cotton.

The emergence time referred to above is with respect to the weeds. In the post-emergence selective use, the compounds of the invention may be applied pre-emergence the crops but it is generally preferred to effect the application post-emergence both the weeds and crop.

The compounds may be and preferably are employed as herbicidal compositions in association with herbicidally acceptable diluent(s). Suitable formulations contain 0.01% to 99% by weight of active ingredient, from 0 to 20% herbicidally acceptable surfactant and 1 to 99.99% solid or liquid diluent(s). Higher ratios of surfactant to active ingredient are sometimes desirable and are achieved by incorporation into the formulation or by tank mixing. Application forms of composition generally contain between 0.01 and 25% by weight of active ingredient. Lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful formulations of the compounds of the invention include dusts, granules, pellets, suspension concentrates, wettable powders, emulsifiable concentrates and the like. They are obtained by conventional manner, e.g. by mixing the compounds of the invention with the diluent(s). More specifically liquid compositions are obtained by mixing the ingredients, fine solid compositions by blending and, usually grinding, suspensions by wet milling and granules and pellets by spraying the active material onto preformed granular carriers or by agglomeration techniques.

Alternatively, the compounds of the invention may be used in microencapsulated form.

Herbicidally acceptable additives may be employed in the herbicidal compositions to improve the performance of the active ingredient and to reduce foaming, caking and corrosion.

Surfactant as used herein means a herbicidally acceptable material which imparts emulsifiability, spreading, wetting, dispersibility or other surface-modifying properties. Examples of surfactants are sodium lignin sulphonate and lauryl sulphate.

Diluents as used herein mean a liquid or solid herbicidally acceptable material used to dilute a concentrated material to a usable or desirable strength. For dusts or granules it can be e.g. talc, kaolin or diatomaceous earth, for liquid concentrate forms, for example a hydrocarbon such as xylene or an alcohol such as isopropanol, and for liquid application forms i.a. water or diesel oil.

Further information regarding solid diluents, liquid diluents and solvents, surfactants, preparation of suspensions, agglomeration techniques and art of herbicidal formulation is given or referred to in the U.K. Patent Application No. 2,015,503, page 19 to 20.

The compositions of this invention can also comprise other compounds having biological activity, e.g. compounds having similar or complementary herbicidal activity or compounds having plant growth regulating, herbicidal, antidotal, fungicidal or insecticidal activity.

Insofar as the production of any starting material is not particularly described, these compounds are known, or may be produced in accordance with processes known for the preparation of 2-amino-4-hydroxypyrimidine derivatives and of cyclopropylmethylhalogenides or in a manner analogous to processes described herein or to known processes.

Specific Examples of herbicidal compositions will now be described.

EXAMPLE A: Wettable Powder

25 Parts of a compound of the invention, e.g. the compound of Example 1 hereinafter given are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE B: Emulsion Concentrate

25 Parts of a compound of the invention, e.g. the compound of Example 1 hereinafter given, 65 parts of xylene and 10 parts of emulsifier (e.g. ATLOX 4851 B a blend of Ca alkylarylsulphonate and a polyethoxylated triglyceride of Atlas Chemie GmbH) are thoroughly mixed until a homogeneous solution is obtained. The resulting emulsion concentrate is diluted with water before use.

EXAMPLE C: Granules

5 Kg of a compound of the invention, e.g. the compound of Example 1 hereinafter given, are dissolved in 15 l methylene chloride. The solution is then added to 95 kg of granulated attapulgite (mesh size 24/28 mesh/inch) and thoroughly mixed. The solvent is then evaporated off under reduced pressure.

The invention is further illustrated by the following Examples wherein temperatures are in °C.

FINAL COMPOUNDS

Example 1:
2-Isopropylamino-4-methyl-6-[(1-methyl-2,2-dichlorocyclopropyl)methoxy]pyrimidine 8.4 g (0.05 mol) 2-Isopropylamino-6-hydroxy-6-methylpyrimidine, 6.9 g (0.05 mol) $K_2CO_3$, 6.9 g (0.05 mol) 1-methyl-2,2-dichlorocyclopropylmethylbromide and 100 ml absolute dimethylformamide are charged in a sulphonation flask and the mixture heated for 26 hours at a bath temperature of 110°. After cooling, the reaction mixture is filtered over diatomaceous earth and concentrated. The resulting orange-red oil is chromatographed on silica gel, using diethylether:n-hexane 1:1 as mobile phase. The title compounds is obtained as a yellow, clear oil, Rf value 0.25.

Example 2

Following the procedure of Example 1 but employing appropriate starting materials of formula II and formula III, the following compounds of formula I are obtained. Where the compounds are obtained as an oil, their Rf values on siliga gel are given, whereby (a), (b) and (c) specify the mobile phase used, which is for (a) diethylether:n-hexane 1:1, for (b) diethylether:n-hexane 1:3 and for (c) diethylether:n-pentane 1:3.

| | | Compound of formula I | | | | | | | | |
|---|---|---|---|---|---|---|---|---|---|---|
| Ex. | $R_1$ | $R_2$ | $R_3$ | $R_4$ | $R_5$ | $R_6$ | $R_7$ | $Y_1$ | $Y_2$ | Characterization |
| A | $C_2H_5$ | H | H | H | H | $CH_3$ | H | Cl | Cl | 96–98 |
| B | Allyl | H | H | H | H | $CH_3$ | H | Cl | Cl | 86–88 |

-continued

| | | | | | Compound of formula I | | | | | |
|---|---|---|---|---|---|---|---|---|---|---|
| Ex. | $R_1$ | $R_2$ | $R_3$ | $R_4$ | $R_5$ | $R_6$ | $R_7$ | $Y_1$ | $Y_2$ | Characterization |
| C | 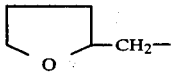 | H | H | H | H | $CH_3$ | H | Cl | Cl | 77–79 |
| D | $CH_3OCH_2CH_2CH_2$ | H | H | H | H | $CH_3$ | H | Cl | Cl | 78–80 |
| E | $n\text{-}C_3H_7$ | H | H | H | H | $CH_3$ | H | Cl | Cl | 77–79 |
| F | $n\text{-}C_3H_7$ | H | $CH_3$ | H | H | $CH_3$ | H | Cl | Cl | 78–80 |
| G | $n\text{-}C_3H_7$ | H | H | $CH_2Cl$ | H | $CH_3$ | H | Cl | Cl | 68–70 |
| H | $n\text{-}C_3H_7$ | H | H | $CH_3$ | H | $CH_3$ | H | Cl | Cl | 93–95 |
| J | $n\text{-}C_3H_7$ | H | $CH_2Cl$ | H | H | $CH_3$ | H | Cl | Cl | 84–86 |
| K | $n\text{-}C_3H_7$ | H | H | $CH_3$ | $CH_3$ | $CH_3$ | H | Cl | Cl | 73–75 |
| L | $i\text{-}C_3H_7$ | H | H | H | H | $CH_3$ | H | Cl | Cl | 49–50 |
| M | $i\text{-}C_3H_7$ | H | H | $CH_3$ | H | $CH_3$ | H | Cl | Cl | oil/0.25a |
| N | $i\text{-}C_3H_7$ | H | H | H | H | $CH_3$ | H | Br | Br | oil/0.15a |
| O | $CH_3OCH_2CH_2$ | H | H | H | H | $CH_3$ | H | Cl | Cl | 76–78 |
| P | $i\text{-}C_3H_7$ | H | H | $CH_3$ | $CH_3$ | $CH_3$ | H | Cl | Cl | oil/0.25a |
| Q | $i\text{-}C_3H_7$ | H | $CH_2Cl$ | H | H | $CH_3$ | H | Cl | Cl | oil/0.25a |
| R | $i\text{-}C_3H_7$ | H | H | H | $CH_2Cl$ | $CH_3$ | H | Cl | Cl | oil/0.25a |
| S | $i\text{-}C_3H_7$ | H | $CH_3$ | H | H | $CH_3$ | H | Br | Br | oil/0.10b |
| T | $n\text{-}C_4H_9$ | H | H | H | H | $CH_3$ | H | Cl | Cl | 77–79 |
| U | $n\text{-}C_4H_9$ | H | $CH_3$ | H | H | $CH_3$ | H | Cl | Cl | 47–49 |
| V | $n\text{-}C_4H_9$ | H | H | $CH_3$ | H | $CH_3$ | H | Cl | Cl | 63–65 |
| W | $n\text{-}C_4H_9$ | H | H | H | H | $CH_3$ | H | Br | Br | 74–76 |
| X | $n\text{-}C_4H_9$ | H | H | $CH_2Cl$ | H | $CH_3$ | H | Cl | Cl | 54–55 |
| Y | $CH_3CH_2(CH_3)CH$ | H | H | H | H | $CH_3$ | H | Cl | Cl | oil/0.25a |
| Z | $CH_3CH_2(CH_3)CH$ | H | $CH_3$ | H | H | $CH_3$ | H | Cl | Cl | oil/0.25a |
| Z-1 | $CH_3CH_2(CH_3)CH$ | H | H | $CH_3$ | H | $CH_3$ | H | Cl | Cl | oil/0.25a |
| Z-2 | $CH_3CH_2(CH_3)CH$ | H | H | H | H | $CH_3$ | H | Br | Br | oil/0.25a |
| Z-3 | $CH_3CH_2(CH_3)CH$ | H | H | $CH_2Cl$ | H | $CH_3$ | H | Cl | Cl | oil/0.35a |
| Z-4 | $tert.C_4H_9$ | H | H | H | H | $CH_3$ | H | Cl | Cl | 72–74 |
| Z-5 | $tert.C_4H_9$ | H | $CH_3$ | H | H | $CH_3$ | H | Cl | Cl | 70–72 |
| Z-6 | $n\text{-}C_5H_9$ | H | H | H | H | $CH_3$ | H | Cl | Cl | 58–60 |
| Z-7 | $n\text{-}C_5H_9$ | H | $CH_3$ | H | H | $CH_3$ | H | Cl | Cl | 50–62 |
| Z-8 | $n\text{-}C_5H_9$ | H | H | $CH_3$ | H | $CH_3$ | H | Cl | Cl | 61–63 |
| Z-9 | $(CH_3)_2CHCH_2CH_2$ | H | H | H | H | $CH_3$ | H | Cl | Cl | 80–82 |
| Z-10 | $CH_3CH_2CH_2(CH_3)CH$ | H | H | H | H | $CH_3$ | H | Cl | Cl | oil/0.25a |
| Z-11 | $CH_3CH_2CH_2(CH_3)CH$ | H | $CH_3$ | H | H | $CH_3$ | H | Cl | Cl | oil/0.30a |
| Z-12 | $CH_3CH_2CH_2(CH_3)CH$ | H | H | $CH_3$ | H | $CH_3$ | H | Cl | Cl | oil/0.15b |
| Z-13 | $CH_3CH_2CH_2(CH_3)CH$ | H | H | $CH_2Cl$ | H | $CH_3$ | H | Cl | Cl | oil/0.25a |
| Z-14 | $(CH_3)_2\text{—}CH_2\text{—}CH(CH_3)\text{—}$ | H | H | H | H | $CH_3$ | H | Cl | Cl | oil/0.25b |
| Z-15 | $(C_2H_5)_2CH$ | H | H | H | H | $CH_3$ | H | Cl | Cl | oil/0.15a |
| Z-16 |  | H | H | H | H | $CH_3$ | H | Cl | Cl | 48–49 |
| Z-17 |  | H | $CH_3$ | H | H | $CH_3$ | H | Cl | Cl | oil/0.25a |
| Z-18 |  | H | H | $CH_3$ | H | $CH_3$ | H | Cl | Cl | oil/0.20a |
| Z-19 | $n\text{-}C_6H_{13}$ | H | H | H | H | $CH_3$ | H | Cl | Cl | 52–53 |
| Z-20 | $n\text{-}C_6H_{13}$ | H | $CH_3$ | H | H | $CH_3$ | H | Cl | Cl | 46–48 |
| Z-21 | $n\text{-}C_6H_{13}$ | H | H | H | $CH_3$ | $CH_3$ | H | Cl | Cl | 48–50 |
| Z-22 | $(CH_3)_2CHCH_2CH(CH_3)\text{—}$ | H | H | H | H | $CH_3$ | H | Cl | Cl | oil/0.10b |
| Z-23 | $(C_2H_5)_2CHCH_2$ | H | H | H | H | $CH_3$ | H | Cl | Cl | 61–63 |

-continued

Compound of formula I

| Ex. | R₁ | R₂ | R₃ | R₄ | R₅ | R₆ | R₇ | Y₁ | Y₂ | Characterization |
|---|---|---|---|---|---|---|---|---|---|---|
| Z-24 | cyclohexyl-CH₂ (C₆H₁₁—CH₂) | H | H | H | H | CH₃ | H | Cl | Cl | 84–86 |
| Z-25 | n-C₅H₁₁—CH(CH₃)— | H | H | H | H | CH₃ | H | Cl | Cl | oil/0.30a) |
| Z-26 | n-C₅H₁₁—CH(CH₃)— | H | CH₃ | H | H | CH₃ | H | Cl | Cl | oil/0.25c) |
| Z-27 | n-H₁₅C₇ | H | H | H | H | CH₃ | H | Cl | Cl | 45–47 |
| Z-28 | n-H₁₅C₇ | H | CH₃ | H | H | CH₃ | H | Cl | Cl | oil/0.15b) |
| Z-29 | n-H₁₅C₇ | H | H | CH₃ | H | CH₃ | H | Cl | Cl | oil/0.20b) |
| Z-30 | n-H₁₇C₈ | H | H | H | H | CH₃ | H | Cl | Cl | 43–45 |
| Z-31 | n-H₁₇C₈ | H | CH₃ | H | H | CH₃ | H | Cl | Cl | oil/0.25a) |
| Z-32 | n-H₁₃C₆—CH(CH₃)— | H | H | H | H | CH₃ | H | Cl | Cl | oil/0.25a) |
| Z-33 | (CH₃)₂CH(CH₂)₃—CH(CH₃)— | H | H | H | H | CH₃ | H | Cl | Cl | oil/0.30a) |
| Z-34 | n-H₉C₄CH(C₂H₅)—CH₂ | H | H | H | H | CH₃ | H | Cl | Cl | oil/0.15b) |
| Z-35 | n-C₉H₁₉ | H | H | H | H | CH₃ | H | Cl | Cl | 45–47 |
| Z-36 | n-C₉H₁₉ | H | CH₃ | H | H | CH₃ | H | Cl | Cl | oil/0.35a) |
| Z-37 | n-C₁₀H₂₁ | H | H | H | H | CH₃ | H | Cl | Cl | 35–37 |
| Z-38 | n-C₁₀H₂₁ | H | CH₃ | H | H | CH₃ | H | Cl | Cl | oil/0.10b) |
| Z-39 | n-C₁₁H₂₃ | H | H | H | H | CH₃ | H | Cl | Cl | 35–37 |
| Z-40 | n-C₁₈H₃₇ | H | H | H | H | CH₃ | H | Cl | Cl | 43–45 |
| Z-41 | n-C₁₈H₃₇ | H | CH₃ | H | H | CH₃ | H | Cl | Cl | 44–46 |
| Z-42 | i-C₃H₇ | H | H | H | H | CH₃ | CH₃ | Cl | Cl | oil/0.10b) |
| Z-43 | n-C₃H₇ | H | H | H | H | CH₃ | nC₃H₇ | Cl | Cl | oil/0.25a) |
| Z-44 | i-C₃H₇ | H | H | H | H | CH₃ | iC₃H₇ | Cl | Cl | oil/0.15b) |
| Z-45 | H | H | H | H | H | CH₃ | H | Cl | Cl | 109–111 |
| Z-46 | CH₃ | H | H | H | H | CH₃ | H | Cl | Cl | 126–127 |
| Z-47 | C₂H₅ | H | CH₃ | H | H | CH₃ | H | Cl | Cl | 62–64 |
| Z-48 | C₂H₅ | H | CH₃ | H | H | CH₃ | H | Br | Br | 98–100 |
| Z-49 | n-C₃H₇ | H | H | H | H | CH₃ | H | Br | Br | 85–88 |
| Z-50 | n-C₃H₇ | H | CH₃ | H | H | CH₃ | H | Br | Br | 57–59 |
| Z-51 | n-C₄H₉ | H | CH₃ | H | H | CH₃ | H | Br | Br | 49–51 |
| Z-52 | (CH₃)₂CH—CH₂ | H | H | H | H | CH₃ | H | Cl | Cl | 100–102 |
| Z-53 | (CH₃)₂CH—CH₂ | H | CH₃ | H | H | CH₃ | H | Cl | Cl | 65–67 |
| Z-54 | CH₃—CH₂—CH(CH₃)— | H | H | H | H | CH₃ | H | Br | Br | oil/0.30a) |
| Z-55 | Cl₂C(cyclopropyl)—CH₂ | H | H | H | H | CH₃ | H | Cl | Cl | 64–66 |
| Z-56 | Cl₂C(cyclopropyl)—CH₂ | H | CH₃ | H | H | CH₃ | H | Cl | Cl | oil/0.20a) |
| Z-57 | n-C₅H₉ | H | CH₃ | H | H | CH₃ | H | Br | Br | 42–44 |
| Z-58 | CH₃—(CH₂)₂—CH(CH₃)— | H | CH₃ | H | H | CH₃ | H | Br | Br | oil/0.30a) |
| Z-59 | (CH₃)₂—CH—CH(CH₃)— | H | CH₃ | H | H | CH₃ | H | Cl | Cl | oil/0.30a) |
| Z-60 | n-C₆H₁₃ | H | CH₃ | H | H | CH₃ | H | Br | Br | 52–54 |

-continued

| | Compound of formula I | | | | | | | | | |
|---|---|---|---|---|---|---|---|---|---|---|
| Ex. | $R_1$ | $R_2$ | $R_3$ | $R_4$ | $R_5$ | $R_6$ | $R_7$ | $Y_1$ | $Y_2$ | Characterization |
| Z-61 | $(CH_3)_2CHCH_2CH(CH_3)$ | H | $CH_3$ | H | H | $CH_3$ | H | Br | Br | oil/0.30a) |
| Z-62 | $CH_3-CH(CH_3)-CH_2-CH(CH_3)$ | H | $CH_3$ | H | H | $CH_3$ | H | Cl | Cl | oil/0.30a) |
| Z-63 | cyclohexyl | H | H | H | H | $CH_3$ | H | Cl | Cl | oil/0.10b) |
| Z-64 | cyclohexyl | H | $CH_3$ | H | H | $CH_3$ | H | Cl | Cl | oil/0.25a) |
| Z-65 | n-$C_7H_{15}$ | H | H | $CH_2Cl$ | H | $CH_3$ | H | Cl | Cl | 43-45 |
| Z-66 | n-$C_7H_{15}$ | H | $CH_3$ | H | H | $CH_3$ | H | Br | Br | oil/0.25a) |
| Z-67 | n-$C_5H_{11}$-CH($CH_3$)- | H | $CH_3$ | H | H | $CH_3$ | H | Br | Br | oil/0.30a) |
| Z-68 | (i-$C_3H_7$)$_2$-CH | H | H | H | H | $CH_3$ | H | Cl | Cl | oil/0.20b) |
| Z-69 | (i-$C_3H_7$)$_2$-CH | H | $CH_3$ | H | H | $CH_3$ | H | Cl | Cl | oil/0.35a) |
| Z-70 | n-$C_6H_{13}$-CH($CH_3$)- | H | $CH_3$ | H | H | $CH_3$ | H | Cl | Cl | oil/0.40a) |
| Z-71 | n-$C_6H_{13}$-CH($CH_3$)- | H | $CH_3$ | H | H | $CH_3$ | H | Br | Br | oil/0.35a) |
| Z-72 | n-$C_6H_{13}$-CH($CH_3$)- | H | H | $CH_2Cl$ | H | $CH_3$ | H | Cl | Cl | oil/0.35a) |
| Z-73 | n-$C_{10}H_{21}$ | H | H | $CH_3$ | H | $CH_3$ | H | Cl | Cl | oil/0.10b) |
| Z-74 | n$C_8H_{17}CH=CH(CH_2)_8$ | H | H | H | H | $CH_3$ | H | Cl | Cl | oil/0.25a) |
| Z-75 | n$C_8H_{17}CH=CH(CH_2)_8$ | H | H | $CH_3$ | H | $CH_3$ | H | Br | Br | oil/0.35a) |
| Z-76 | $CH_3$ | $CH_3$ | H | H | H | $CH_3$ | H | Cl | Cl | oil/0.35b) |
| Z-77 | $CH_3$ | $CH_3$ | $CH_3$ | H | H | $CH_3$ | H | Cl | Cl | 54-56 |
| Z-78 | n-$C_3H_7$ | n-$C_3H_7$ | H | H | H | $CH_3$ | H | Cl | Cl | oil/0.45b) |
| Z-79 | n-$C_3H_7$ | n-$C_3H_7$ | $CH_3$ | H | H | $CH_3$ | H | Cl | Cl | oil/0.55b) |
| Z-80 | ($CH_2)_4$ | | H | H | H | $CH_3$ | H | Cl | Cl | 72-73 |
| Z-81 | ($CH_2)_4$ | | $CH_3$ | H | H | $CH_3$ | H | Cl | Cl | oil/0.20b) |
| Z-82 | ($CH_3)_2CH-CH(CH_3)-$ | H | $CH_3$ | H | H | $CH_3$ | H | Br | Br | oil/0.35a) |
| Z-83 | i-$C_3H_7$ | H | H | H | H | $CH_3$ | H | H | H | 41-43 |
| Z-84 | n-$C_5H_{11}$- | H | H | $CH_2Cl$ | H | $CH_3$ | H | Cl | Cl | oil/0.25a) |
| Z-85 | ($CH_3)_2CH-CH(CH_3)-$ | H | H | $CH_2Cl$ | H | $CH_3$ | H | Cl | Cl | oil/0.30a) |
| Z-86 | n-$C_{10}H_{21}$- | H | $CH_3$ | H | H | $CH_3$ | H | Br | Br | oil/0.25a) |
| Z-87 | $CH_3CH_2CH_2CH(CH_3)-$ | H | H | H | H | $CH_3$ | H | Br | Br | oil/0.25a) |
| Z-88 | n-$C_9H_{19}$- | H | H | H | H | $CH_3$ | H | Br | Br | oil/0.25a) |

The hydrogen oxalate of the compound of Example 2L, m.p. 120°–122°, is obtained as follows:

In a sulfonation flask is charged 4.5 g oxalic acid in 200 ml absolute diethyl ether and thereto added, dropwise, a solution of 14.5 g of compound 2L, in base form, in 50 ml absolute diethyl ether. The temperature rises thereby from 21° to 24°. The mixture is then stirred over night at room temperature. The resulting hydrogen oxalate is filtered off, washed with absolute diethyl ether and dried under vacuum.

INTERMEDIATES

Example 3: 2,2-Dichlorocyclopropylmethylbromide

To a sulphonation flask containing 242 g (2 mol) allylbromide, 954 g (8 mol) $CHCl_3$ and 6 g benzyl-triethylammonium bromide are dropped, whilst stirring, 640 g 50% (8 mol) NaOH. The temperature is kept, by partial cooling, at about 40° to 45°. When the addition is completed, the reaction mixture is stirred 2 hours and a further 2 hours at a bath temperature of 55°. The reaction mixture is then cooled, diluted with 1 water and extracted with $CH_2Cl_2$. The organic phase is dried over $Na_2SO_4$ and the solvent then evaporated. The resulting brown liquid is distilled over a Vigreux column (length 20 cm) to yield a colourless liquid, b.p. 73°–83°.

TEST RESULTS

Example 4: Weed control-Pre-emergence treatment

Seed pots (7 cm diameter) are filled with a mixture of peat culture sulstrate and sand. The exposed surface of the peat culture sulstrate and sand mixture is sprayed with a test liquid of a test compound (e.g. formulated in accordance with Example B) and seeds of *Lepidium sativum, Agrostis alba, Avena sativa* and *Lolium perenne* are sown in each pot, whereby the *Avena sativa* and *Lolium perenne* seeds are, after sowing covered with a thin layer (0.5 cm) of peat culture sulstrate/sand mixture. The pots are kept for 21 days at room temperature with 14 to 17 hours light (daylight or its equivalent) per day.

Determination of the herbicidal effect of the particular herbicide is made after the 21 day period. The determination involves a visual evaluation of the degree and quality of damage to the various seed plants.

The compounds of formula I of the above Examples 1 and 2 are applied in the above manner at dosages equivalent to 1.4 and 5.6 kg of active agent/hectare.

Herbicidal activity is observed, that is to say, significant damage to the test plants is observed.

Example 5: Weed control-Post-emergence treatment

A procedure similar to that employed in Example 4 is followed with the exception that the test compounds (herbicides) are applied when the plants are at the 2–4 leaf stage, the sowing of the plant seeds being staggered to ensure that the plants reach the 2–4 leaf stage at about the same time.

Again the compounds are applied in the above manner at dosages corresponding to 1.4 kg/ha and 5.6 kg/ha. The determination of the herbicidal effect is made 21 days after application of the test compounds and involves an analogous evaluation as described in Example 4. A herbicidal activity is observed.

EXAMPLE 6

The following Tables A and B will reflect a further evaluation of representative compounds of the invention in the following pre-emergence test procedure.

Seed dishes measuring 30×40 cm are filled to a depth of 6 cm with a mixture of peat culture substrate and sand. The exposed surface of the peat culture substrate and sand mixture is sprayed with an aqueous test liquid (e.g. formulated in accordance with Example B) comprising a compound of the invention in a given concentration. The spray volume corresponds to 600 l aqueous test liquid/ha. The same test is repeated with various concentrations of test liquid, whereby the concentrations are selected in such a manner that the application rates indicated on the following tables are realised. Six species of seed are then sown in each dish. The number of seeds sown for each plant species depends on the seed germination potential and also the initial growth size of the particular seed plant. After sowing of the seeds, the treated surface is covered with a thin layer about 0.5 cm deep of the peat culture and sand mixture.

The prepared seed dishes are kept for 28 days at a temperature of 20° to 24° C. and 14 to 17 hours light each day.

Determination of the herbicidal effect of the particular herbicide is made after the 28 day period. The determination involves a visual evaluation of the degree and quality of damage to the various seed plants.

Particularly good-pre-emergence selective herbicidal activity is observed i.a. with the compound of Example 1 in cotton and sunflower, with the compound of Example 2E in cotton, sunflower and carrot, with the compound of Example 2L in cotton and sunflower, with the compound of Example 2Y in cotton, alfalfa, carrot, potato and sunflower, and with the compound of Example 2R in bean, carrot, cotton, potato, soya and sugar beet. The compounds of the Examples 1, 3E, 3L, 3Y and 3z-83 showed also a good activity against *Galium aparine*.

TABLE A

| | Pre-emergence application 1 kg/ha | | | | | | | |
|---|---|---|---|---|---|---|---|---|
| Plant | Compound I Tested - % damage | | | | | | | |
| treated | 2E | 2L | 2N | 2R | 2W | 2Y | 1 | 2Z-83 |
| Amaran. retrofl. | 100 | 100 | 100 | 80 | 40 | 70 | 90 | 100 |
| Capsella b.p. | 90 | 100 | 100 | 70 | 10 | 100 | 90 | 100 |
| Chenop. alb. | 100 | 100 | 80 | 40 | 10 | 100 | 100 | 100 |
| Galium aparine | 70 | 60 | 10 | 10 | 10 | 70 | 30 | 50 |
| Senecio vulg. | 70 | 60 | 20 | 10 | 0 | 20 | 20 | 100 |
| Stellaria media | 60 | 90 | 20 | 50 | 0 | 40 | 20 | 80 |
| Alfalfa | 20 | 70 | 20 | 30 | 0 | 20 | 10 | 100 |
| Bean | 20 | 0 | 60 | 20 | 0 | 20 | 20 | 30 |
| Carrot | 40 | 40 | 0 | 0 | 0 | 30 | 20 | 60 |
| Cotton | 40 | 0 | 0 | 0 | 0 | 10 | 0 | 0 |
| Flax | 50 | 100 | 100 | 60 | 20 | 70 | 60 | 100 |
| Potato | 20 | 20 | 0 | 0 | 0 | 20 | 10 | 30 |
| Soya | 20 | 60 | 30 | 0 | 0 | 20 | 10 | 80 |
| Sugar beet | 30 | 20 | 0 | 0 | 0 | 10 | 20 | 70 |
| Rape | 60 | 100 | 90 | 60 | 30 | 90 | 40 | 100 |
| Sunflower | 10 | 0 | 0 | 0 | 0 | 20 | 10 | 0 |
| Agropyron repens | 20 | 80 | 40 | 10 | 0 | 20 | 40 | 40 |
| Agrostis alba | 60 | 90 | 90 | 60 | 20 | 90 | 80 | 80 |
| Alopec. myos. | 70 | 90 | 80 | 50 | 30 | 70 | 70 | 100 |
| Apera sp. venti. | 90 | 100 | 100 | 60 | 10 | 80 | 90 | 90 |
| Avena fatua | 70 | 80 | 50 | 50 | 0 | 60 | 80 | 100 |
| Echinochloa c.g. | 70 | 90 | 80 | 60 | 0 | 70 | 60 | 70 |
| Corn | 40 | 80 | 80 | 30 | 30 | 50 | 40 | 70 |
| Wheat | 20 | 50 | 60 | 10 | 10 | 10 | 30 | 60 |

TABLE B

| | Pre-emergence application 5 kg/ha | | | | | | | |
|---|---|---|---|---|---|---|---|---|
| Plant | Compound I Tested - % damage | | | | | | | |
| treated | 2E | 2L | 2N | 2R | 2W | 2Y | 1 | 2Z-83 |
| Amaran. retrofl. | 100 | 100 | — | 100 | 100 | 100 | 100 | 100 |
| Capsella b.p. | 100 | 90 | — | 100 | 90 | 100 | 100 | 100 |
| Chenop. alb. | 100 | 100 | — | 100 | 30 | 100 | 100 | 100 |
| Galium aparine | 90 | 100 | — | 30 | 10 | 80 | 100 | 100 |
| Senecio vulg. | 70 | 100 | — | 20 | 0 | 60 | 60 | 100 |
| Stellaria media | 90 | 100 | — | 60 | 10 | 90 | 90 | 100 |
| Alfalfa | 80 | 100 | — | 80 | 20 | 30 | 70 | 100 |
| Bean | 40 | 80 | — | 30 | 10 | 40 | 40 | 100 |
| Carrot | 20 | 40 | — | 0 | 0 | 30 | 40 | 100 |
| Cotton | 10 | 30 | — | 10 | 0 | 0 | 0 | 0 |
| Flax | 100 | 100 | — | 100 | 40 | 100 | 100 | 100 |
| Potato | 40 | 80 | — | 0 | 0 | 0 | 40 | 70 |
| Soya | 40 | 90 | — | 20 | 10 | 70 | 40 | 100 |
| Sugar beet | 100 | 100 | — | 10 | 0 | 80 | 50 | 100 |
| Rape | 100 | 100 | — | 80 | 40 | 100 | 100 | 100 |
| Sunflower | 0 | 20 | — | 0 | 0 | 10 | 10 | 70 |
| Agropyron repens | 70 | 80 | — | 20 | 0 | 60 | 60 | 90 |

TABLE B-continued

| | Pre-emergence application 5 kg/ha | | | | | | | |
|---|---|---|---|---|---|---|---|---|
| Plant | Compound I Tested - % damage | | | | | | | |
| treated | 2E | 2L | 2N | 2R | 2W | 2Y | 1 | 2Z-83 |
| *Agrostis alba* | 90 | 100 | — | 70 | 80 | 90 | 100 | 100 |
| *Alopec. myos.* | 90 | 100 | — | 90 | 70 | 90 | 90 | 100 |
| *Apera sp. venti.* | 100 | 100 | — | 100 | 60 | 100 | 100 | 100 |
| *Avena fatua* | 100 | 100 | — | 70 | 20 | 90 | 90 | 100 |
| *Echinochloa c.g.* | 80 | 100 | — | 70 | 40 | 90 | 90 | 90 |
| Corn | 70 | 80 | — | 70 | 70 | 70 | 90 | 90 |
| Wheat | 90 | 90 | — | 30 | 30 | 40 | 70 | 100 |

— not tested

Example 7: Post-emergence Treatment

The following Tables C and D will reflect a further evaluation of representative compounds of the formula I in a post-emergence test procedure similar to that of the pre-emergence test described in Example 6, except that the herbicide test liquid is applied when the seeds are at a 2-4 leaf stage. For that purpose the various seed species are sown in time-staggered relationship. The greenhouse conditions (temperature, light) are as in Example 6. Determination of the herbicidal effect is also effected 28 days after application according to the method of Example 6.

According to the test data listed in Tables C and D, the compound of Example 1 is particularly indicated for post-emergence herbicidal treatment in rice and potato and the compounds of Examples 2E and 2Y for post-emergence herbicidal treatment in wheat, cotton and potato.

TABLE C

| | Post-emergence application 1 kg/ha | | | | | | | |
|---|---|---|---|---|---|---|---|---|
| Plant | Compound I Tested - % damage | | | | | | | |
| treated | 2E | 2L | 2N | 2R | 2W | 2Y | 1 | 2Z-83 |
| *Amaran. retrofl.* | 90 | 100 | 100 | 100 | 100 | 80 | 60 | 80 |
| *Capsella b.p.* | 100 | 100 | 100 | 100 | 100 | 100 | 100 | 100 |
| *Chenop. alb.* | 80 | 90 | 90 | 90 | 80 | 100 | 90 | 100 |
| *Galium aparine* | 80 | 50 | 30 | 50 | 30 | 60 | 30 | 20 |
| *Senecio vulg.* | 100 | 90 | 70 | 30 | 20 | 40 | 10 | 100 |
| *Stellaria media* | 100 | 90 | 80 | 20 | 30 | 40 | 10 | 90 |
| Alfalfa | 10 | 30 | 30 | 10 | 10 | 10 | 10 | 30 |
| Bean | 90 | 100 | 100 | 100 | 90 | 90 | 90 | 100 |
| Carrot | 30 | 10 | 10 | 10 | 20 | 20 | 10 | 30 |
| Cotton | 20 | 100 | 100 | 100 | 100 | 90 | 80 | 100 |
| Flax | 100 | 100 | 100 | 100 | 100 | 100 | 100 | 100 |
| Potato | 10 | 50 | 70 | 50 | 10 | 20 | 20 | 20 |
| Soya | 90 | 80 | 100 | 100 | 80 | 70 | 80 | 90 |
| Sugar beet | 100 | 90 | 80 | 100 | 90 | 80 | 90 | 80 |
| Rape | 90 | 100 | 100 | 100 | 100 | 100 | 100 | 100 |
| Sunflower | 10 | 30 | 100 | 10 | 10 | 80 | 10 | 20 |
| *Agropyron repens* | 0 | 10 | 10 | 0 | 0 | 10 | 10 | 0 |
| *Agrostis alba* | 100 | 100 | 90 | 90 | 90 | 90 | 100 | 100 |
| *Alopec. myos.* | 20 | 80 | 80 | 70 | 80 | 40 | 90 | 80 |
| *Apera sp. venti.* | 20 | 50 | 90 | 80 | 30 | 20 | 10 | 80 |
| *Avena fatua* | 10 | 30 | 60 | 40 | 10 | 30 | 20 | 20 |
| *Echinochloa c.g.* | 100 | 100 | 100 | 90 | 90 | 100 | 90 | 90 |
| Corn | 20 | 30 | 20 | 10 | 10 | 10 | 10 | 30 |
| Wheat | 10 | 10 | 0 | 0 | 0 | 0 | 10 | 0 |

TABLE D

| | Post-emergence application 5 kg/ha | | | | | | | |
|---|---|---|---|---|---|---|---|---|
| Plant | Compound I Tested - % damage | | | | | | | |
| treated | 2E | 2L | 2N | 2R | 2W | 2Y | 1 | 2Z-83 |
| *Amaran. retrofl.* | 100 | 100 | 100 | 100 | 100 | 100 | 100 | 100 |
| *Capsella b.p.* | 100 | 100 | 100 | 100 | 100 | 100 | 100 | 100 |
| *Chenop. alb.* | 100 | 100 | 100 | 100 | 100 | 100 | 100 | 100 |
| *Galium aparine* | 90 | 100 | 90 | 90 | 70 | 100 | 100 | 100 |
| *Senecio vulg.* | 100 | 100 | 100 | 100 | 100 | 100 | 100 | 100 |
| *Stellaria media* | 100 | 100 | 100 | 100 | 100 | 100 | 80 | 100 |
| Alfalfa | 40 | 100 | 100 | 90 | 10 | 80 | 70 | 100 |
| Bean | 100 | 100 | 100 | 100 | 100 | 70 | 100 | 100 |
| Carrot | 70 | 90 | 90 | 30 | 30 | 80 | 30 | 100 |
| Cotton | 100 | 100 | 100 | 90 | 100 | 100 | 100 | 100 |
| Flax | 100 | 100 | 100 | 100 | 100 | 100 | 100 | 100 |
| Potato | 70 | 90 | 100 | 90 | 10 | 50 | 30 | 100 |
| Soya | 90 | 90 | 100 | 100 | 100 | 80 | 90 | 100 |
| Sugar beet | 100 | 100 | 100 | 100 | 100 | 100 | 100 | 100 |
| Rape | 100 | 100 | 100 | 100 | 100 | 100 | 100 | 100 |
| Sunflower | 50 | 70 | 80 | 60 | 20 | 100 | 100 | 100 |
| *Agropyron repens* | 10 | 30 | 10 | 10 | 10 | 10 | 10 | 10 |
| *Agrostis alba* | 100 | 100 | 100 | 100 | 100 | 100 | 100 | 100 |
| *Alopec. myos.* | 90 | 100 | 100 | 90 | 100 | 100 | 100 | 100 |
| *Apera sp. venti.* | 90 | 100 | 100 | 100 | 90 | 100 | 100 | 100 |
| *Avena fatua* | 90 | 100 | 100 | 100 | 80 | 100 | 100 | 100 |
| *Echinochloa c.g.* | 100 | 100 | 100 | 100 | 100 | 100 | 100 | 100 |
| Corn | 40 | 70 | 100 | 100 | 40 | 100 | 100 | 100 |
| Wheat | 10 | 50 | 10 | 10 | 0 | 20 | 60 | 10 |

Example 8: Pre-emergence Treatment

Selectivity in Cotton

Seed boxes (length 15 cm, breadth 13 cm, depth 7 cm) are filled with sandy soil, containing ca. 1% organic matter and seeds of the test species sown therein. The seeds are then covered with a thin layer (about 0.2 to 0.5 cm) of sand, wetted and then sprayed with various concentrations of an aqueous test liquid of a test compound, whereby the amount of spray liquor applied is equivalent to an application rate of 600 l test liquid pro hectare.

In the following Table E the herbicidal activity is given for dosages equivalent to the application rates indicated in the table; the indicated herbicidal activity is the mean value of 3 tests and is determined 28 days after application by visual degree and quality of damage to the various seed plants.

TABLE E

| Compound | kg a.i./ha | % Damage | | | | | | | |
| | | CD | CS | Am | Ab | Ga | Ec | Di | So | Le |
|---|---|---|---|---|---|---|---|---|---|---|
| 1 | 0.15 | 0 | 0 | 97 | 47 | 40 | 100 | 100 | 100 | 100 |

TABLE E-continued

| Compound | kg a.i./ha | % Damage | | | | | | | | |
|---|---|---|---|---|---|---|---|---|---|---|
| | | CD | CS | Am | Ab | Ga | Ec | Di | So | Le |
| | 0.3 | 10 | 10 | 100 | 67 | 57 | 100 | 100 | 100 | 100 |
| | 0.6 | 13 | 13 | 100 | 83 | 70 | 100 | 100 | 100 | 100 |
| 2E | 0.15 | 0 | 0 | 100 | 47 | 47 | 90 | 93 | 90 | 97 |
| | 0.3 | 0 | 0 | 100 | 67 | 60 | 100 | 97 | 97 | 100 |
| | 0.6 | 10 | 10 | 100 | 87 | 77 | 100 | 100 | 97 | 100 |
| 2L | 0.15 | 0 | 7 | 93 | 67 | 47 | 100 | 100 | 93 | 100 |
| | 0.3 | 10 | 10 | 100 | 90 | 63 | 100 | 100 | 97 | 100 |
| | 0.6 | 10 | 10 | 100 | 100 | 77 | 100 | 100 | 100 | 100 |
| 2N | 0.15 | 0 | 3 | 100 | 33 | 50 | 100 | 100 | 97 | 100 |
| | 0.3 | 13 | 13 | 100 | 73 | 60 | 100 | 100 | 97 | 100 |
| | 0.6 | 17 | 17 | 100 | 90 | 73 | 100 | 100 | 100 | 100 |
| 2Y | 0.15 | 7 | 7 | 90 | 43 | 47 | 97 | 97 | 93 | 100 |
| | 0.3 | 7 | 7 | 100 | 63 | 60 | 100 | 100 | 97 | 100 |
| | 0.6 | 17 | 17 | 100 | 83 | 70 | 100 | 100 | 100 | 100 |
| 2Z-83 | 0.15 | 0 | 0 | 87 | 37 | 50 | 97 | 87 | 87 | 83 |
| | 0.3 | 0 | 0 | 100 | 67 | 63 | 100 | 100 | 90 | 100 |
| | 0.6 | 10 | 10 | 100 | 80 | 83 | 100 | 100 | 97 | 100 |
| FLUOMETURON | 0.15 | 0 | 0 | 97 | 40 | 37 | 87 | 60 | 83 | 67 |
| | 0.3 | 0 | 7 | 100 | 67 | 57 | 93 | 67 | 87 | 87 |
| | 0.6 | 0 | 7 | 100 | 100 | 77 | 100 | 90 | 93 | 100 |

CD = Cotton, Deltapine variety
CS = Cotton, Stoneville variety
Am = Amaranthus
Ab = Galium
Ec = Echinochloa
Di = Digitaria sang.
So = Sorghum hal.
Le = Leptochloa dubia.
Fluometuron: cotton herbicide (see Pesticide Manual, by H. Martin et.al., 5th Ed., page 277).

Example 9: Pre-emergence Treatment

Selectivity in sunflower

The seeds of the test species were sown and treated analogous to Example 8, and the results determined 28 days after application by visual degree and quality of damage to the various seed plants. The results are given in Table F for dosages equivalent to the application rates indicated in the table.

TABLE F

| Compound | kg a.i./ha | % Damage | | | | | | |
|---|---|---|---|---|---|---|---|---|
| | | SF | Am | Ch | Ga | Av | Ec | Al |
| 1 | 0.6 | 10 | 100 | 97 | 37 | 100 | 100 | 100 |
| | 1.2 | 20 | 100 | 100 | 73 | 100 | 100 | 100 |
| | 2.4 | 23 | 100 | 97 | 77 | 100 | 100 | 100 |
| 2E | 0.6 | 13 | 100 | 97 | 53 | 100 | 100 | 100 |
| | 1.2 | 23 | 100 | 97 | 90 | 100 | 100 | 100 |
| | 2.4 | 27 | 100 | 97 | 90 | 100 | 100 | 100 |
| 2L | 0.6 | 33 | 100 | 90 | 73 | 100 | 100 | 100 |
| | 1.2 | 53 | 100 | 90 | 87 | 100 | 100 | 100 |
| | 2.4 | 57 | 100 | 90 | 90 | 100 | 100 | 100 |
| 2Y | 0.6 | 13 | 100 | 97 | 43 | 100 | 100 | 100 |
| | 1.2 | 13 | 100 | 97 | 57 | 100 | 100 | 100 |
| | 2.4 | 20 | 100 | 97 | 83 | 100 | 100 | 100 |
| TER-BUTRYNE | 0.6 | 60 | 100 | 93 | 83 | 97 | 100 | 100 |
| | 1.2 | 100 | 100 | 100 | 83 | 97 | 100 | 100 |
| | 2.4 | 97 | 100 | 100 | 93 | 100 | 100 | 100 |

Meaning of abbreviations, so far not already given:
SF = Sunflower
Ch = Chenopodium
Av = *Avena fatua*
Al = Alopecurus
TERBUTRYNE: selective herbicide, recommended for use in sunflower (Pesticide Manual, 5th Ed., by H. Martin et.al, page 493).

What is claimed is:
1. A compound of formula I,

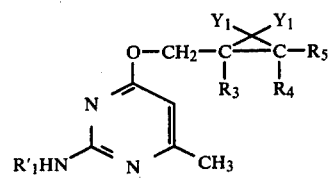

wherein
either $R_1$ is H or $(C_{1-18})$alkyl, $(C_{1-18})$alkyl substituted by up to 2 substituents selected from $(C_{1-4})$alkoxy or 2-tetrahydrofuryl; $(C_{1-18})$alkenyl; $(C_{3-8})$-cycloalkyl or $(C_{3-8})$cycloalkyl-$(C_{1-5})$alkyl, unsubstituted or substituted by up to 2 halogens selected from fluorine, chlorine and bromine; phenyl unsubstituted or substituted by up to 3 substituents selected from halogen of the group fluorine, chlorine and bromine $(C_1-C_4)$alkyl and $(C_1-C_4)$alkoxy;
and $R_2$ is H, $(C_1-C_5)$alkyl,
or $R_1$ and $R_2$ together are a $(C_4-C_6)$alkylene chain,
$Y_1$ and $Y_2$ independently are H or halogen selected from fluorine, chlorine or bromine,
$R_3$, $R_4$ and $R_5$ independently are H, $(C_1-C_5)$alkyl unsubstituted or substituted by halogen selected from fluorine, chlorine or bromine,
$R_6$ is $(C_1-C_5)$alkyl, and
$R_7$ is H or $(C_1-C_5)$alkyl in free base or acid addition salt form.

2. A compound according to claim 1 of formula Ia, $$\begin{array}{c} Y_1 \diagup\hspace{-0.3em}\diagdown Y_1 \\ O-CH_2-C-C-R_5 \\ | \quad | \\ R_3 \quad R_4 \end{array} \quad \text{Ia}$$

$$R'_1HN \diagdown N \diagup CH_3$$

wherein $R_1'$ is $(C_{1-18})$alkyl, and $Y_1$, $R_3$, $R_4$ and $R_5$ are as defined in claim 1, in free base or acid addition salt form.

3. A compund according to claim 2, selected from the group consisting of compounds wherein $R_1'$, $Y_1$, $R_3$, $R_4$ and $R_5$, are
(a) $CH(CH_3)_2$, Cl, $CH_3$, H and H respectively
(b) n-$C_3H_7$, Cl, H, H and H respectively
(c) $CH(CH_3)_2$, Cl H, H and H respectively
(d) $CH(CH_3)_2$, Br, H, H and H respectively
(e) 2-$C_4H_9$, Cl, H, H and H respectively
(f) $CH(CH_3)_2$, H, H, H and H respectively in free base or acid addition salt form.

4. A herbicide, comprising a compound as claimed in claim 1, in free base or herbicidally acceptable acid addition salt form, and an herbicidally acceptable diluent.

5. A method of combatting weeds, which comprises applying thereto or to the locus thereof a herbicidally effective amount of a compound of claim 1, in free base or herbicidally acceptable acid addition salt form.

6. A method of combatting weeds in a crop locus, which comprises applying to said locus a selective herbicidally effective amount of a compound of claim 1, in free base or herbicidally acceptable acid addition salt form.

7. A method according to claim 6, wherein the compound is applied pre-emergence and wherein the crop is cotton or sunflower.

* * * * *